US008962874B2

(12) United States Patent
Chong et al.

(10) Patent No.: US 8,962,874 B2
(45) Date of Patent: *Feb. 24, 2015

(54) PROCESS FOR FRACTIONATING CRUDE TRIGLYCERIDE OIL

(71) Applicant: Malaysian Palm Oil Board (MPOB), Kajang, Selangor Darul Ehsan (MY)

(72) Inventors: Chiew Let Chong, Kajang (MY); Chee Beng Yeoh, Kajang (MY)

(73) Assignee: Malaysian Palm Oil Board (MPOB), Kajang (MY)

( * ) Notice: Subject to any disclaimer, the term of this patent is extended or adjusted under 35 U.S.C. 154(b) by 8 days.

This patent is subject to a terminal disclaimer.

(21) Appl. No.: 14/025,679

(22) Filed: Sep. 12, 2013

(65) Prior Publication Data

US 2014/0296550 A1 Oct. 2, 2014

(30) Foreign Application Priority Data

Apr. 1, 2013 (MY) ........................... PI 2013001143

(51) Int. Cl.
*C07C 51/43* (2006.01)
*C11B 3/00* (2006.01)

(52) U.S. Cl.
CPC .................................... *C11B 3/008* (2013.01)
USPC ........................................................ 554/211

(58) Field of Classification Search
USPC ........................................................ 554/211
See application file for complete search history.

(56) References Cited

U.S. PATENT DOCUMENTS

| | | | |
|---|---|---|---|
| 4,795,569 | A | 1/1989 | Higuchi et al. |
| 5,045,243 | A | 9/1991 | Kuwabara et al. |
| 5,602,265 | A | 2/1997 | Kommer et al. |
| 2002/0018841 | A1 | 2/2002 | Bons et al. |
| 2002/0031577 | A1 | 3/2002 | Arends et al. |

FOREIGN PATENT DOCUMENTS

| | | | | |
|---|---|---|---|---|
| EP | 1 028 159 A1 | 8/2000 | | |
| EP | 1028159 A1 * | 8/2000 | ................ C11B 7/00 | |

* cited by examiner

*Primary Examiner* — Deborah D Carr
(74) *Attorney, Agent, or Firm* — Maschoff Brennan

(57) ABSTRACT

The present invention relates to an improved process for fractionating triglyceride oil. The process according to the present invention attains a reproducible crystallization by introducing a controlled temperature profile and ensuing crystal development that reduce the amount of entrapped olein inside the crystals or crystal aggregates. The process of the present invention may be used to fractionate vegetable oils such as palm oil or its blends with other palm oil products or edible vegetable oils.

4 Claims, No Drawings

PROCESS FOR FRACTIONATING CRUDE TRIGLYCERIDE OIL

FIELD OF INVENTION

The present invention relates to a process for fractionating crude triglyceride oil. More particularly, it relates to a process for fractionating crude triglyceride oil obtained from edible vegetable oils which is semi solid ambient at temperature of between 0 to 40° C.

BACKGROUND OF INVENTION

Triglyceride oils contain undesirable minor components or impurities including free saturated fatty acids, such as palmitic or stearic acids, and other suspended matter that, unless removed, render the oil commercially unsuitable in that they produce a soapy taste or a strong flavor. Such unrefined oils are generally refined by one or several of the following steps: degumming, neutralizing or alkali refining to reduce the fatty acid content thereof, bleaching, dewaxing and deodorization.

The main source of haziness and discoloration in triglyceride oil is the presence of crystallized triglycerides with saturated fatty acids such as palmitic or stearic acids. These triglycerides with saturated fatty acids crystallize and agglomerate producing a haze and also precipitate creating a turbid product. Another cause of haziness in the oil is the presence of other dispersed solids like protein and mucilaginous materials of microscopic size. Precipitated matter, such as proteins, can cause deterioration of the oil. When these microscopic materials agglomerate they become visible and produce unsightly haze in the final oil product. The haziness due to crystallized saturated fat is not very aesthetically pleasant. This is detrimental, particularly in cosmetics and pharmaceuticals, since it is important for the oil to be very clear and translucent for appealing to the customers.

In the field of oil processing, fractionation almost always refers to the mechanical separation of the liquid from the solid, crystallized, constituents of given oil. The split between liquid and solid fractions depend on the temperature at which crystallization is conducted.

Fractionation is a process that has been known in the industry for more than a century. Earlier the olein and stearin fractions had been separated by settling, using only the force of gravity to bring about a separation between the heavier solid phase and the lighter liquid phase. Naturally this method of fractionation left the settled solid phase containing large quantities of entrained or trapped liquid oil, certainly more than 75%.

In the latter years a process of this type, using only indirect cooling of the oil but separating liquid from solid by filter or centrifuge, developed known as “dry fractionation”.

Vegetable oils especially palm oil is fractionated in one- or two-stage by utilizing the difference in melting points of respective components, there has been known instances, solvent fractionation using organic solvent such as acetone, hexane, or the like, detergent fractionation using a surfactant, dry fractionation, sweating and the like.

Among these, solvent fractionation is advantageous because fractionation can be carried out precisely. However, on the other hand, this is dangerous, since a flammable solvent is used, and also requires high production costs. In addition, solvent fractionation is not the most effective process for the fractionation of raw materials such as coconut oil, palm kernel oil and fat.

The method of detergent fractionation has inferior precision of fractionation and its products have inferior quality in comparison with those fractionated using solvent fractionations. Furthermore, separation of oil from an aqueous solution containing a surfactant and treatment of waste water containing a surfactant are troublesome and incomplete.

The method of dry fractionation requires expensive crystallization tank facilities. In addition, productivity, fractionation efficiency and quality of a product are inferior to those of the above two methods.

Application of the sweating method is limited to certain kinds of fats and oils. That is, it is employed for removing wax but is not suitable for fractionation of oils or fats.

Dry fractionation involves the heating up of palm oil to a temperature of between 50 to 55° C., cooling the oil to between 30 to 40° C. followed by further cooling of the oil to the final fractionation temperature of between 20 to 25° C. The crystallizer is then held at this temperature for a number of hours depending on the type and characteristics of the olein and stearin desired. The crystallized slurry is then filtered under a pressure to obtain the olein and stearin fractions. The yield of olein and stearin obtained is between 75 to 80% and 20 to 25% respectively.

If the holding times, the number of fractionation steps or the filtration pressure is varied the characteristics of the olein and stearin obtained could be altered. The iodine value (IV) of the olein obtained is about 56 for a single fractionation of around 10 hours holding time at the final fractionation temperature and a filtration pressure of 3 to 5 bars.

Dry fractionation of crude palm oil using the conditions stated above is deemed to be difficult to control due to the presence of gums and other impurities which will interfere with the crystallization of the oil during the fractionation process.

At present the fractionation of crude palm oil is carried out using the wet detergent process. An aqueous solution of sodium lauryl sulphate is added and the mixture is cooled to crystallize the stearin. The slurry is then centrifuged to separate the solid from the liquid phase. Water is then removed from the olein phase and also the detergent is removed at the same time. This process is completely different from that of dry fractionation. It may be very difficult to completely remove all the detergent from the olein phase and there may be trace quantities of the detergent left. In view of the mounting emphasis on food safety in the future, this process will be less and less appealing. It is noted and widely accepted in the industry that dry fractionation of crude palm oil will result in low olein yield and the dry fractionation process is rather difficult to be controlled.

U.S. Pat. No. 4,795,569 to Higuchi et al. describes a process in which the oil is introduced into a filter chamber and allowed to crystallize inside that chamber by circulating a coolant such as water through the space between the membrane and a filter frame. However, this process requires filter cloth to be sealed first with coagula of the material to be treated. This makes it a lengthy process that makes inefficient use of the expensive membrane press.

Accordingly, an improvement has been described in U.S. Pat. No. 5,045,243 to Kuwabara et al. in which the oil or fat to be fractionated is first of all solidified in trays to form solid blocks which are then crushed to yield a pumpable paste that is then introduced into a membrane press to separate this paste into an olein fraction and a stearin fraction. The solidification process is commonly carried out in cooling tunnels. However, these have the disadvantage that the oil is exposed to the air while being in process and that it is virtually impossible to control the rate of cooling inside the individual trays.

European Patent Application 1.028.59 by Yoneda et al. disclosed a stationary crystallization. The oil or fat to be fractionated is not solidified into a solid block, but the crystallization process is halted when the partially crystallized mass is still sufficiently fluid to be pumped into the membrane filter press. However, this means that the material to be fractionated has to be diluted with olein before being cooled.

U.S. Patent Application No. 2002/0018841 discloses preparation of a blend of triglycerides involving a dry fractionation method in which high stearic, and high oleic sunflower oil is heated to at least 65° C., cooling the liquefied oil to 35° C. at a rate of 1° C./minute, followed by further cooling to 20° C. at rate of 1.5° C./minute, further slow cooling to and stabilization at 5 to 20° C. This method will result in a large amount of olein to be trapped in the solid crystals of varying sizes.

U.S. Pat. No. 5,602,265 discloses a process for triglyceride oil fractionation using a crystallization modifying substance which is a copolymer. Said copolymer is added to oil or to the solution of the oil. The present invention does not involve use of copolymer as mentioned in the prior art. This process will result in a inhomogeneous distribution of crystal sizes resulting in a large quantity of the liquid olein to be occluded in the stearin.

U.S. Patent Application No. 2002/0031577 discloses a process for crystallization of a solid phase from a liquid, wherein the liquid during crystallization is subjected to ultrasound in the absence of transient cavitation. The present invention does not involve use of ultrasound waves, which increases the cost of the process. Ultrasound will increase the nucleation rate and impedes crystal growth, resulting in fine crystals, making the separation of the olein from the stearin due to clogging during the filtration process.

SUMMARY OF INVENTION

It is therefore an object of the present invention to provide a process for fractionation of vegetable oil preferably palm oil which can improve the efficiency of dry fractionation.

A further object of the present invention is to attain a reproducible crystallization by introducing a controlled temperature profile during cooling and the ensuing crystal development.

Another object of the present invention is to provide an improved process of dry fractionation that reduce the amount of entrained or entrapped olein inside the crystals or crystal aggregates.

It is also an object of the present invention to provide a process of dry fractionation that produces a favorable crystal form to ease the filtration process and minimal olein entrapment.

According to the present invention, the process for fractionating crude triglyceride oil which is semi solid at a temperature of between 0 to 40° C., wherein the triglyceride oil is obtained from an edible vegetable oil, the process includes the steps of (a) heating the triglyceride oil to a temperature range of between 55 to 70° C. for a period of about 1 minute to 3 hours, (b) cooling the triglyceride oil obtained from step (a) to a temperature range of between 20 to 30° C. for a period of about 1 minute to 5 hours such that the triglyceride oil is at least partially crystallized thereby forming crystallized slurries, (c) warming the crystallized triglyceride oil from step (b) to a temperature in the range of between 22 to 33° C. for a period of about 1 minute to 3 hours, (d) cooling the triglyceride oil obtained from step (c) to a temperature range of between 10 to 30° C. for a period of about 1 minute to 65 hours and (e) removing the crystallized slurries which is at a temperature in the range of between 10 to 30° C. for a period of about 1 minute to 65 hours.

The method according to the present invention, wherein said heating the triglyceride oil of step (a) results in said triglyceride oil having a temperature in the range of approximately 55 to 70° C. for a period in the range of about 1 minute to 3 hours.

Cooling the triglyceride oil of step (b) results in said triglyceride oil having a temperature in the range of 28-40° C. for a period in the range of about 1 minute to 3 hours and further cooling of the triglyceride oil results in said triglyceride oil having a temperature in the range of about 20 to 30° C. for a period in range of about 1 minute to 5 hours.

In step (c), the triglyceride oil is warmed to a temperature in the range of about 22 to 33° C. in a period in the range of about 1 minute to 3 hours.

Crystallizing of step (e) is performed at a temperature in the range of about 10 to 30° C. for a period in the range of about 1 minute to 65 hours.

In an embodiment of the invention, removing of crystallized slurry is conducted using filtration to obtain olein fraction and stearin fraction.

DETAILED DESCRIPTION OF THE PREFERRED EMBODIMENTS

According to the present invention, there is provided a process for fractionating crude triglyceride oil which is semi solid at a temperature of between 0 to 40° C., wherein the triglyceride oil is obtained from an edible vegetable oil, the process includes the steps of (a) heating the triglyceride oil to a temperature range of between 55 to 70° C. for a period of about 1 minute to 3 hours, (b) cooling the triglyceride oil obtained from step (a) to a temperature range of between 20 to 33° C. for a period of about 1 minute to 5 hours such that the triglyceride oil is at least partially crystallized thereby forming crystallized slurries, (c) warming the crystallized triglyceride oil from step (b) to a temperature in the range of between 22 to 30° C. for a period of about 1 minute to 3 hours, (d) cooling the triglyceride oil obtained from step (c) to a temperature range of between 10 to 30° C. for a period of about 1 minute to 65 hours and (e) removing the crystallized slurries which is at a temperature in the range of between 10 to 30° C. for a period of about 1 minute to 65 hours.

In a preferred embodiment of the invention, triglyceride oil is palm oil, or other vegetable oil either in its natural state or in a state after processing and or modifications.

In a preferred embodiment of the present invention, palm oil is crude palm oil, refined, bleached or deodorized palm oil or blends of palm oil or products with other palm oil products or with other edible vegetable oils.

In the preferred embodiment of the present invention, crude palm oil is heated to a temperature of approximately 55 to 70° C. and held for a period in the range of about 1 minute to 3 hours at this temperature to thoroughly destroy all traces of previous thermal history.

The heated oil is then cooled to a temperature of approximately 20 to 40° C. for a period of between 1 to 3 hours. In the preferred embodiments of the present invention, the cooling process can be conducted in two stages i.e. in stage 1, the heated oil is cooled to a temperature of approximately 28 to 40° C. and held at this temperature for a period in the range of about 1 minute to 3 hours. The oil is then further cooled to a fractionation temperature of between 20 to 30° C. The oil is then held at this fractionation temperature until the oil crystals start to appear. The crystallizing slurry is then allowed to crystallize further for a period in the range of about 1 minute to 5 hours.

After that, the temperature of the crystallizing slurry is increased to a temperature in the range of 22 to 33° C. Upon reaching this temperature, the crystallizing slurry is kept at this temperature for a period of time in the range of about 1 minute to 3 hours. After this period the temperature of the crystallizing slurry is lowered to a temperature in the range of 10 to 30° C. in a period in the range of 1 minute to 3 hours and held at this temperature for a period in the range of about 1 minute to 65 hours.

The crystallizing slurry is then filtered under a pressure of 2 to 60 bars in a membrane or any other type of filter or filtration to obtain the olein and stearin fractions.

The present invention can be distinguished from the previous state of the art in the step whereby the temperature of the crystallizing slurry is increased from the final fractionation temperature in the range of 10 to 30° C. after the appearance of the oil crystals and a holding period in the range of about 1 minute to 5 hours, to a temperature in the range of 22 to 33° C. where it is held for a period in the range of about 1 minute to 3 hours before the temperature of the said slurry is returned to the final fractionation temperature in the range of 10 to 30° C. and held for a period in the range of about 1 minute to 65 hours.

Smaller crystals in the crystallizing slurry will dissolve and grow on the existing larger and harder crystals. This will result in coarse, large and hard crystals, which are easily filtered and are able to withstand the filtration pressure. This will also reduce the amount of entrained or entrapped olein inside the crystals or crystal aggregates. $\beta'$ (beta-prime) crystals are obtained by in the temperature range of 20 to 35° C. as verified by X-ray diffraction of the crystals obtained for crude palm oil crystals. This is the desired crystal form for easy filtration and minimal olein entrapment. The dry fractionation condition applied in the present invention can be used for the dry fractionation of crude palm oil and their fractions, in the case of multiple fractionations, with olein yield of between 70 to 85% and stearin yield of 15 to 30% from laboratory results for the first fractionation. The iodine value (IV) of the olein obtained from the method according to the present invention is between 56 to 60 Wij and the IV of the stearin is between 30 to 45 Wij for a single fractionation step with a holding time of around ten hours and using vacuum filtration. If the holding times are extended, the number of fractionations can be increased. The same concepts embodied in this present invention can be applied at each step.

It is to be understood that the present invention may be embodied in other specific forms and is not limited to the sole embodiment described above. However modifications and equivalents of the disclosed concepts such as those which readily occur to one skilled in the art are intended to be included within the scope of the claims which are appended thereto.

EXAMPLE

An experiment was conducted to fractionate a crude triglyceride oil as per the present invention.

The steps involved in this process:

a) heating the triglyceride oil 65° C. for 30 minutes;
b) cooling the triglyceride oil to 30° C. for 75 mins;
c) further cooling the triglyceride oil to 24° C. for 60 mins until the triglyceride oil is at least partially crystallized thereby forming crystallized slurries;
d) warming the crystallized triglyceride oil from step (c) to 27° C. for 15 mins;
e) cooling the triglyceride oil obtained from step (d) to 24° C. for 10 mins
f) allowing further crystallizing at 24° C. for 80 mins; and
g). removing the crystallized slurries.

It is noted that the yield of olein obtained from laboratory vacuum filtration system is 77.1% as compared to the control without steps (d) to (f) where the yield obtained is only 74.2%.

The invention claimed is:

1. A process for fractionating crude triglyceride oil which is semi solid at a temperature of between 0 to 40° C., wherein the triglyceride oil is obtained from an edible vegetable oil, the process includes the steps of:

(a) heating the triglyceride oil to a temperature range of between 55 to 70° C. for a period of about 1 minute to 3 hours;
(b) cooling the triglyceride oil obtained from step (a) to a temperature range of between 20 to 30° C. for a period of about 1 minute to 5 hours such that the triglyceride oil is at least partially crystallized thereby forming crystallized slurries;
(c) warming the crystallized triglyceride oil from step (b) to a temperature in the range of between 22 to 33° C. for a period of about 1 minute to 3 hours;
(d) cooling the triglyceride oil obtained from step (c) to a temperature range of between 10 to 30° C. for a period of about 1 minute to 65 hours; and
(e) removing the crystallized slurries which is at a temperature in the range of between 10 to 30° C. for a period of about 1 minute to 65 hours.

2. The process according to claim 1, wherein said vegetable oil is palm oil, or other edible vegetable oil either in its natural state or after processing and or modifications.

3. The process according to claim 2, wherein said palm oil is crude palm oil, refined, bleached or deodorized palm oil, or blends of palm oil or products with other palm oil products or with other edible vegetable oils.

4. The process according to claim 1, wherein said removing of crystallized slurry is conducted using filtration to obtain olein fraction and stearin fraction at a pressure of 5 to 50 bars.

* * * * *